(12) United States Patent
Kim et al.

(10) Patent No.: US 9,051,596 B2
(45) Date of Patent: Jun. 9, 2015

(54) METHOD FOR SCREENING INHIBITORY SUBSTANCES TO INFLAMMATORY SKIN-AGING

(75) Inventors: Ji Seong Kim, Yongin-si (KR); Jin Young Lee, Yongin-si (KR); Jun Seong Park, Yongin-si (KR); Hyang Tae Choi, Yongin-si (KR); Han Byul Kim, Yongin-si (KR); Ji Hyun Bae, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 0 days.

(21) Appl. No.: 14/111,464

(22) PCT Filed: Apr. 13, 2012

(86) PCT No.: PCT/KR2012/002825
§ 371 (c)(1),
(2), (4) Date: Oct. 11, 2013

(87) PCT Pub. No.: WO2012/141531
PCT Pub. Date: Oct. 18, 2012

(65) Prior Publication Data
US 2014/0038220 A1 Feb. 6, 2014

(30) Foreign Application Priority Data

Apr. 13, 2011 (KR) .................. 10-2011-0034299

(51) Int. Cl.
*C12Q 1/37* (2006.01)
*G01N 33/50* (2006.01)

(52) U.S. Cl.
CPC ............... *C12Q 1/37* (2013.01); *G01N 33/502* (2013.01); *G01N 2333/8146* (2013.01); *G01N 2500/10* (2013.01)

(58) Field of Classification Search
CPC .................................................. G01N 33/502
USPC ................................................... 435/4, 7.21
See application file for complete search history.

(56) References Cited

U.S. PATENT DOCUMENTS

2006/0234297 A1 10/2006 Hayashi et al.
2007/0172957 A1 7/2007 Fanton et al.

FOREIGN PATENT DOCUMENTS

WO 03057211 7/2003
WO 2007004771 1/2007

OTHER PUBLICATIONS

William Wu, et al., "Sites of Collagenase Cleavage and Denaturation of Type II Collagen in Aging and Osteoarthritic Articular Cartilage and Their Relationship to the Distribution of Matrix Metalloproteinase 1 and Matrix Metalloproteinase 13," Arthritis & Rheumatism, vol. 46, No. 8, Aug. 2002, pp. 2087-2094.
Kamala P. Sundararaj, et al., "Simvastatin suppresses LPS-induced MMP-1 expression in U937 mononuclear cells by inhibiting protein isoprenylation-mediated ERK activation," Journal of Leukocyte Biology, vol. 84, Oct. 2008, p. 1120-1129.
Written Opinion—PCT/KR2012/002825 dated Nov. 28, 2012.
International Search Report—PCT/KR2012/002825 dated Nov. 28, 2012.
Anca Sindrilaru, et al., "An unrestrained proinflammatory M1 macrophage population induced by iron impairs wound healing in humans and mice", The Journal of Clinical Investigation, vol. 121, No. 3l, Mar. 2011, p. 985-997.
CN Office Action—CN Application No. 201280028652.5 dated Oct. 31, 2014, citing WO 2007004771A1 and "An unrestrained proinflammatory M1 macrophage population induced by iron impairs wound healing in humans and mice."

*Primary Examiner* — Bin Shen
(74) *Attorney, Agent, or Firm* — Cantor Colburn LLP (57) ABSTRACT

Disclosed is a method for screening a substance inhibiting inflammatory skin aging, comprising: treating an immune cell with an inflammatory stimulant; treating a skin cell with a candidate substance; treating the skin cell treated with the candidate substance, with the immune cell treated with the inflammatory stimulant; and measuring the concentration of matrix metalloproteinase-1 (MMP-1) in the skin cell treated with the immune cell.

7 Claims, 12 Drawing Sheets

METHOD FOR SCREENING INHIBITORY SUBSTANCES TO INFLAMMATORY SKIN-AGING

TECHNICAL FIELD

The present disclosure relates to a method for screening a substance inhibiting inflammatory skin aging.

BACKGROUND ART

In general, chronic skin inflammation is a major cause of wrinkles since it reduces elasticity of skin. Once inflammation occurs in skin, the inflammatory site often turns dark brown because of increased pigmentation of melanin. Such inflammatory response facilitates skin aging. The aged skin is vulnerable to various skin infections because of reduced immunity, especially the immunity of skin cells, and the prevalence of autoimmune skin disease also increases due to increased autoantibodies in the serum. In addition, the number of Langerhans cells is smaller in the intrinsically aged skin than in the skin of young people and the number is much smaller in the photoaged skin. Accordingly, the aged skin is highly likely to develop inflammations even under weak stimulation and the inflammation triggers skin aging again. In this way, the vicious cycle goes on.

DISCLOSURE

Technical Problem

The present disclosure is directed to providing an effective method for screening a substance inhibiting inflammatory skin aging.

Technical Solution

In a general aspect, there is provided a method for screening a substance inhibiting inflammatory skin aging, comprising: treating an immune cell with an inflammatory stimulant; treating a skin cell with a candidate substance; treating the skin cell treated with the candidate substance, with the immune cell treated with the inflammatory stimulant; and measuring the concentration of matrix metalloproteinase-1 (MMP-1) in the skin cell treated with the immune cell.

Advantageous Effects

A method for screening a substance inhibiting inflammatory skin aging according to an aspect of the present disclosure is capable of effectively screening a substance inhibiting inflammatory skin aging. Since the method according to the present disclosure determines inhibition of matrix metalloproteinase-1 (MMP-1) which is not a general MMP-1 but induced by inflammatory cytokines, a substance inhibiting inflammatory skin aging can be screened more accurately. Also, since an inflammatory cytokine which is not a specific cytokine but produced by actually stimulating an immune cell is used, a substance inhibiting inflammatory skin aging with higher biological correlation can be screened. Further, since inhibition of MMP-1 production complexly induced by several inflammatory cytokines can be judged at once, a substance inhibiting inflammatory skin aging can be screened more conveniently and effectively.

BEST MODE

In the present disclosure, the term "skin" is used in the broadest concept and means the tissue that covers the body surface of an animal, comprising not only the covering of the face, body, etc. but also the scalp and hair.

In the present disclosure, the term "inflammatory skin aging" includes skin aging induced or accompanied by inflammation.

Hereinafter, the present disclosure is described in detail.

Cytokines produced in response to inflammation such as TNF-α, IL-1β, etc. activate several inflammation-related signaling pathways by binding to the receptors present on the vascular endothelium. During the process, the expression of cell adhesion molecules is increased and extravasation of inflammatory cells occurs. Following the infiltration of inflammatory cells, there is chemo-attractive activities like several cytokines or chemokines etc. and they move toward the inflammation site, thereby provoking immune response.

Since these inflammatory cytokines induce degradation of collagen by facilitating the expression of matrix metalloproteinases, they play a critical role in skin aging and trigger chain reactions by binding to receptors. Accordingly, if any substance can inhibit the production of inflammatory cytokines and can inhibit the production of matrix metalloproteinase-1 (MMP-1) induced by inflammatory cytokines, it will be able to act as a substance inhibiting inflammatory skin aging.

In an aspect, the present disclosure provides a method for screening a substance inhibiting inflammatory skin aging, comprising: treating an immune cell with an inflammatory stimulant; treating a skin cell with a candidate substance; treating the skin cell treated with the candidate substance, with the immune cell treated with the inflammatory stimulant; and measuring the concentration of MMP-1 in the skin cell treated with the immune cell.

When treated with the inflammatory stimulant, the immune cell produces various inflammatory cytokines. Accordingly, the immune cell treated with the inflammatory stimulant, more specifically a culture medium of the immune cell treated with the inflammatory stimulant includes various inflammatory cytokines. If the skin cell is treated with the immune cell, the expression of MMP-1 which promotes degradation of skin collagen in the skin cell is facilitated by the inflammatory cytokines. As described above, inflammation and production of MMP-1 are the main cause of skin aging and are worse in that, once begun, they continue as a vicious cycle. Accordingly, by pretreating the skin cell with the candidate substance and then treating the skin cell with the immune cell comprising the inflammatory cytokines and measuring the concentration of MMP-1 in the skin cell, it may be determined whether the candidate substance is a substance capable of inhibiting inflammatory skin aging. Since this method screens a substance that inhibits the production of MMP-1 induced by inflammatory cytokines, not just a substance that inhibits the production of general MMP-1, it can be more accurately determined whether the candidate substance is a substance inhibiting inflammatory skin aging.

In an exemplary embodiment of the present disclosure, the cytokines produced by the inflammatory stimulant include various inflammatory cytokine. In another exemplary embodiment of the present disclosure, the cytokines include one or more of GROα (CXCL1, chemokine (C—X—C motif) ligand 1), I-309 (CCL-1, chemokine (C—C motif) ligand 1), sICAM-1 (soluble cell adhesion molecules-1), IL (interleukin)-Iβ, IL-1ra, IL-6, IL-8, IL-23, IP-10, MCP-1 (monocyte chemoattractant protein-1), MIF (macrophage migration inhibitory factor), MIP (macrophage inflammatory protein)-1α, MIP-1β, serpin E1, RANTES (regulated on activation, normal T-cell expressed, and secreted) and TNF (tumor necrosis factor)-α, but are not limited thereto.

In an exemplary embodiment of the present disclosure, the immune cell includes a cell that produces inflammatory cytokines when treated with the inflammatory stimulant. In another exemplary embodiment of the present disclosure, the immune cell includes a THP-1 cell (human acute monocytic leukemia cell line). Mononuclear phagocytes are one of the major cells group that form the immune system, and are known as to perform phagocytosis. Among the phagocytes, those present in the blood are called monocytes and those present in tissues are called macrophages. The THP-1 cell is a monocyte derived from human and can differentiate into a macrophage in tissues. The THP-1 cell can be usefully used in cell experiments because it can be cultured for a long of time. Accordingly, it may be more suitable for the present disclosure.

In an exemplary embodiment of the present disclosure, the skin cell includes a normal human fibroblast (NHF). The fibroblast distributed in the dermis plays an important role in wound healing and proliferates quickly in response to inflammation caused by tissue damage. The fibroblast are the major source of extracellular matrix (ECM) proteins and also produces collagen and fibronectin that form a granulation tissue. Also, it may respond quickly to inflammatory cytokines by forming networks with capillaries or other blood vessels. Accordingly, it may be more suitable for the present disclosure.

In an exemplary embodiment of the present disclosure, the inflammatory stimulant includes a substance that can produce an inflammatory cytokine. In another exemplary embodiment of the present disclosure, the inflammatory stimulant includes a lipopolysaccharide (LPS) and interferon-γ (INF-γ).

The LPS is the major component of the outer membrane of Gram-negative bacteria surrounding the peptidoglycan layer. The LPS transports NF-κB into the nucleus. The NF-κB expresses various genes involved in inflammation and immune response by binding to the promoter site of the genes. Accordingly, the LPS is known to stimulate immunoregulators and inflammation-causing substances in human. The degree of inducing the stimulation varies depending on from which bacteria it is derived. In an exemplary embodiment of the present disclosure, the LPS includes an LPS derived from at least one of *Escherichia coli* and *Salmonella*. In another exemplary embodiment of the present disclosure, the LPS derived from *Escherichia coli* (*E. coli*) includes an LPS derived from at least one of *E. coli* 0111:B4, *E. coli* 055:B5 and *E. coli* EH100. In another exemplary embodiment of the present disclosure, the LPS derived from *Salmonella* includes an LPS derived from at least one of *Salmonella typhosa* (*S. typhosa*) and *Salmonella typhimurium* (*S. typhimurium*).

In an exemplary embodiment of the present disclosure, the concentration of the LPS may be 0.001-20 μM, specifically 0.01-15 μM, more specifically 0.1-10 μM, in order to ensure sufficient production of inflammatory cytokines without cytotoxicity.

In an exemplary embodiment of the present disclosure, the interferon-γ (INF-γ) enhances inflammatory stimulation response by the LPS rather than facilitating the production of inflammatory cytokines by directly mediating inflammatory response. Accordingly, inflammatory cytokines can be produced better when treated together with the LPS and the INF-γ and, as a result, a substance inhibiting inflammatory skin aging can be screened more sensitively.

In an exemplary embodiment of the present disclosure, the concentration of the INF-γ may be 1-2000 UNITs, specifically 5-1500 UNITs, more specifically 10-1000 UNITs, in order to ensure the desired effect of the present disclosure without cytotoxicity.

In an exemplary embodiment of the present disclosure, the method for screening a substance inhibiting inflammatory skin aging may further include, after the measuring of the concentration of the MMP-1 in the skin cell, determining the candidate substance as a substance inhibiting inflammatory skin aging if the concentration of the MMP-1 in the skin cell treated with the candidate substance is lower than the concentration of the MMP-1 in the skin cell not treated with the candidate substance. In another exemplary embodiment of the present disclosure, the method further include determining the candidate substance not as a substance inhibiting inflammatory skin aging if the concentration of the MMP-1 in the skin cell treated with the candidate substance is higher than the concentration of the MMP-1 in the skin cell not treated with the candidate substance. In another exemplary embodiment of the present disclosure, the method may further include determining the candidate substance as a substance having a higher effect of inhibiting inflammatory skin aging as the concentration of the MMP-1 in the skin cell treated with the candidate substance is lower as compared to the concentration of the MMP-1 in the skin cell not treated with the candidate substance.

In an exemplary embodiment of the present disclosure, the candidate substance is a subject substance which is to be determined whether it is a substance inhibiting inflammatory skin aging. In another exemplary embodiment of the present disclosure, the candidate substance may include any natural product, which may be a plant, an extract thereof or a chemically synthesized substance.

Hereinafter, the present disclosure will be described in detail through test examples. However, the following test examples are for illustrative purposes only and it will be apparent to those of ordinary skill in the art that the scope of the present disclosure is not limited by the test examples.

Test Example 1

Identification of Bacteria as Appropriate Source of LPS as Stimulant

Because the degree of inducing the stimulation by an LPS varies depending on from which bacteria it is derived, the following experiment was conducted to select an LPS suitable for screening of a substance inhibiting inflammatory skin aging.

THP-1 cells (acquired from Korean Cell Line Bank) were seeded onto a 6-well plate, with $5\times10^5$ cells per well, and cultured in an RPMI-1640 medium (acquired from Lonza) containing 10% (v/v) FBS, 100 U/mL penicillin and 100 µg/mL streptomycin under the condition of 37° C. and 5% $CO_2$ for 24 hours. Subsequently, the cells were cultured for 24 hours after treating with three kinds of LPS derived from *Escherichia coli* (*E. coli* O111:B4, *E. coli* O55:B5 and *E. coli* EH100) and two kinds of LPS derived from *Salmonella* [*Salmonella typhosa* (*S. typhosa*) and *Salmonella typhimurium* (*S. typhimurium*), acquired from Sigma Aldrich], at concentrations of 0, 0.1 and 1 µg/mL, and with 0, 250, 500 and 1000 UNITs of INF-γ (acquired from Sigma Aldrich). Subsequently, the culture medium was centrifuged at 1000 rpm for 3 minutes and the supernatant was taken and then the concentration of TNF-α in the supernatant was determined using a TNF-α ELISA kit. The result is shown in FIG. 1.

Figure 1:
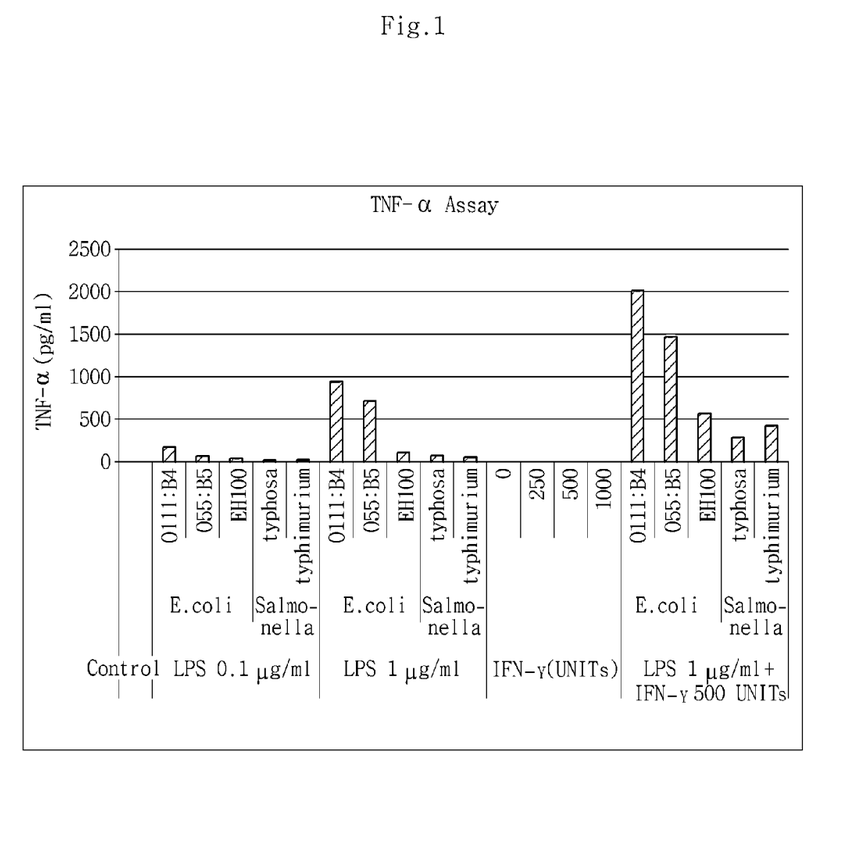
FIG. 1 shows production of TNF-α in a THP-1 cell depending on the concentration of and the kind of lipopolysaccharide (LPS) and the concentration of interferon-γ (INF-γ).

As seen from FIG. 1, when the cells were treated with LPS, the production of TNF-α was in the order of *E. coli* 0111:B4>*E. coli* 055:B5>*E. coli* EH100>*Salmonella typhosa*>*Salmonella typhimurium*, and the order is equally maintained in the case of different concentration of LPS. The absolute production of TNF-α was higher when the cells were treated with 1 µg/mL LPS than with 0.1 µg/mL LPS. Accordingly, it can be seen that the human immune cells are the most sensitive to the LPS derived from *Escherichia coli*, specifically *E. coli* 0111:B4, in the production of inflammatory cytokines.

IFN-γ was found to have no effect on the production of TNF-α at all concentrations. However, when 1 µg/mL LPS was treated together with 500 UNITs of IFN-γ, the production of TNF-α increased remarkably than when the LPS was treated alone, for all the five kinds of LPS. The amount of production was in the order of *E. coli* 0111:B4>*E. coli* 055:B5>*E. coli* EH100>*Salmonella typhimurium*>*Salmonella typhosa*. Accordingly, it can be seen that the IFN-γ enhances the stimulation by the LPS.

Test Example 2

Determination of Optimal Concentration of Stimulant

The following experiment was conducted to determine an optimal concentration for screening of a substance inhibiting inflammatory skin aging.

Figure 3:
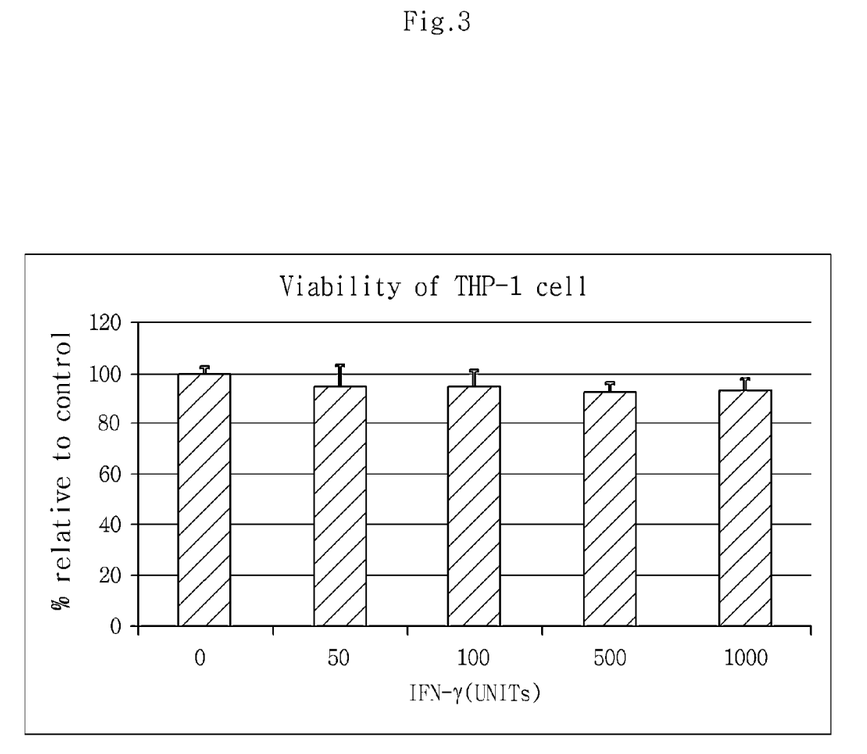
FIG. 3 shows the viability of a THP-1 cell depending on the concentration of INF-γ.
Figure 4:
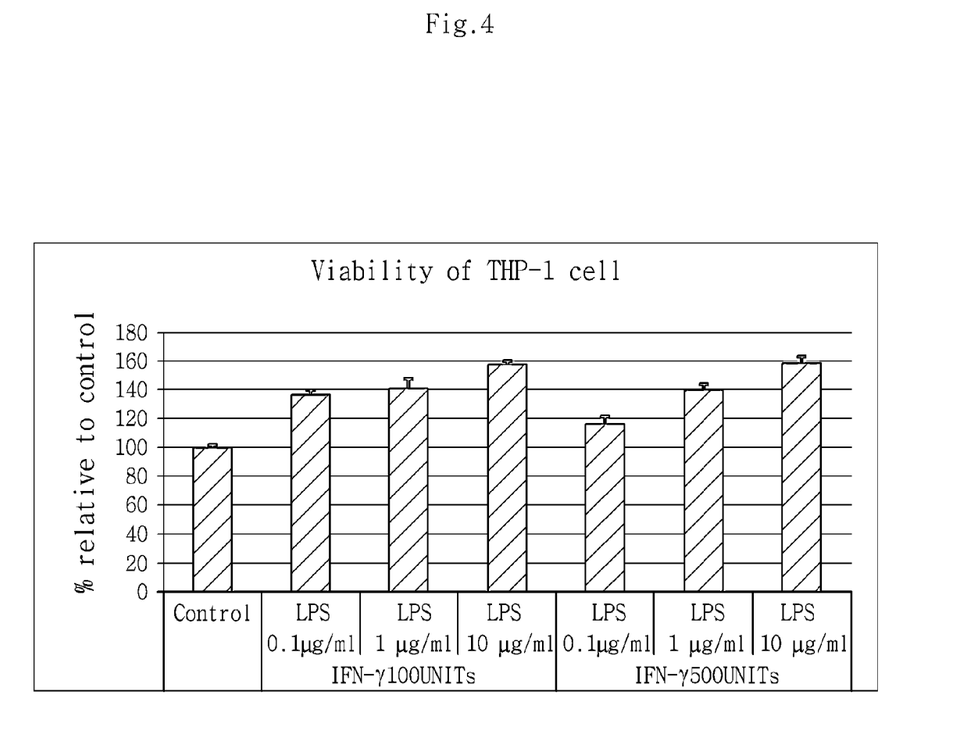
FIG. 4 shows the viability of a THP-1 cell treated with LPS and INF-γ.

THP-1 cells (acquired from Korean Cell Line Bank) were seeded onto a 96-well plate, with $3\times10^4$ cells per well, and cultured in an RPMI-1640 medium (acquired from Lonza) containing 10% (v/v) FBS, 100 U/mL penicillin and 100 µg/mL streptomycin under the condition of 37° C. and 5% $CO_2$ for 24 hours. Subsequently, the cells were cultured for 24 hours after treating with 0, 0.01, 0.1, 1 and 10 µg/mL LPS derived from *Escherichia coli* (*E. coli* 0111:B4, acquired from Sigma Aldrich) and with 0, 50, 100, 500 and 1000 UNITs of IFN-γ (acquired from Sigma Aldrich). After treating with a cell counting kit reagent, with 1/10 the volume of each well, and culturing for 2 hours, cell viability was determined by measuring O.D. value using SpectraMax. The result is shown in FIGS. 2-4.

Figure 2:
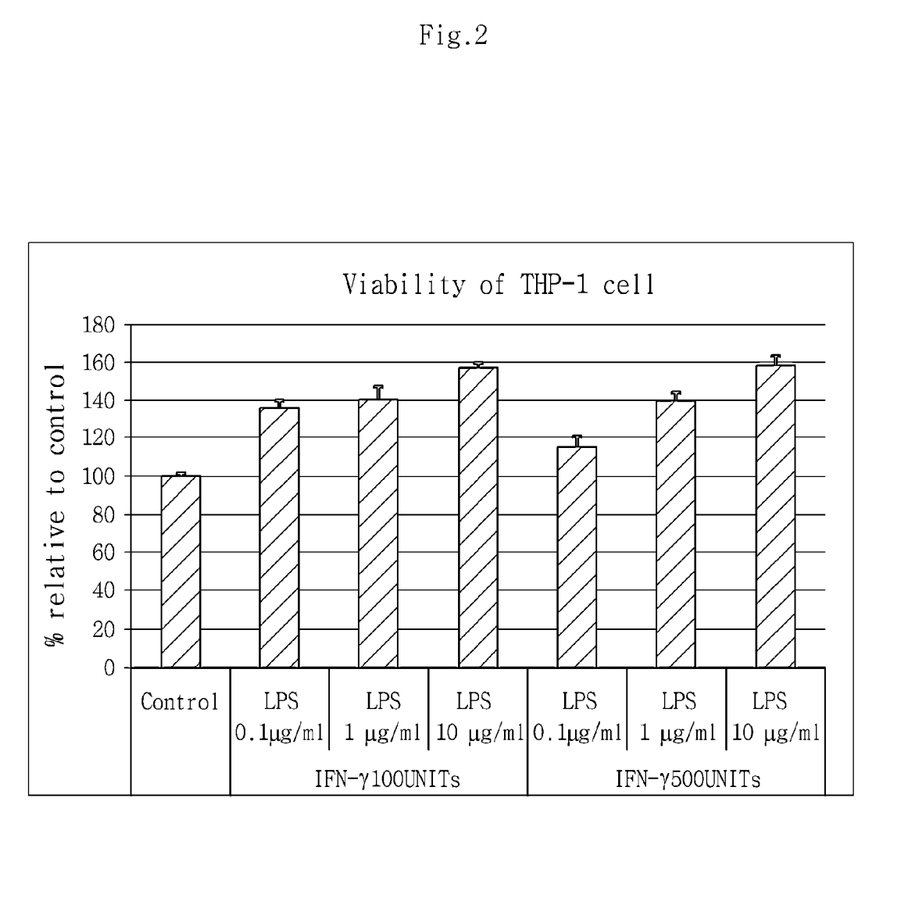
FIG. 2 shows the viability of a THP-1 cell depending on the concentration of LPS.

As seen from FIG. 2, when the cells were treated with 0, 0.01, 0.1, 1 and 10 µg/mL LPS, the proliferation of the cells was promoted in a concentration-dependent manner without cytotoxicity. Also, as seen from FIG. 3, no cytotoxicity was observed when the cells were treated with 0, 50, 100, 500 and 1000 UNITs of IFN-γ. And, as seen from FIG. 4, when the cells were treated with LPS and IFN-γ together, no cytotoxicity was observed and a positive correlation was found between the proliferation of the cells and with the concentration of LPS.

Test Example 3

Confirmation of Production of Inflammatory Cytokines after Treatment with Stimulant The following experiment was conducted to confirm the production of inflammatory cytokines due to inflammatory response upon treatment with a stimulant.

Figure 5:
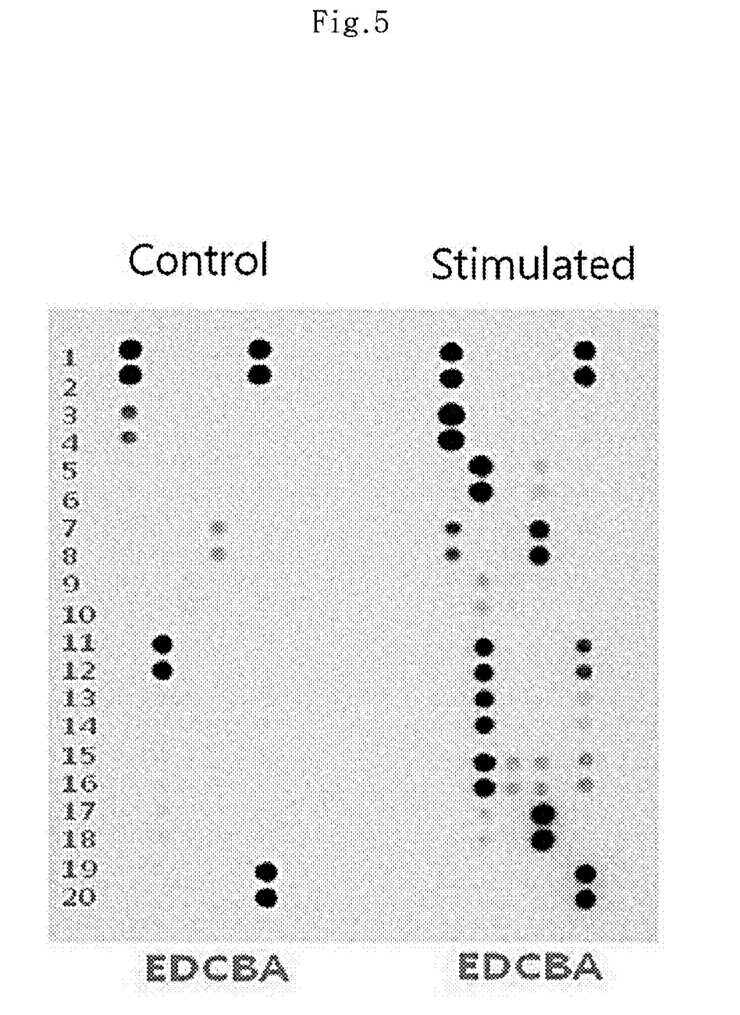
FIG. 5 shows the degree of production of an inflammatory cytokine when treated with LPS and INF-γ.

THP-1 cells (acquired from Korean Cell Line Bank) were seeded onto a 6-well plate, with $5\times10^5$ cells per well, and cultured in an RPMI-1640 medium (acquired from Lonza) containing 10% (v/v) FBS, 100 U/mL penicillin and 100 µg/mL streptomycin under the condition of 37° C. and 5% $CO_2$ for 24 hours. Subsequently, the cells were cultured for 24 hours after treating with 1 µg/mL LPS (derived from *E. coli* 0111:B4, acquired from Sigma Aldrich) and 500 UNITs of IFN-γ (acquired from Sigma Aldrich). The culture medium was centrifuged at 1000 rpm for 3 minutes and the supernatant was taken and then the kind of inflammatory cytokines which is increased as compared to the control group in the supernatant were identified using a cytokine array kit. FIG. 5 shows the expression level of inflammatory cytokines and the inflammatory cytokines for the respective coordinates are described in the following table.

TABLE 1

| Coordinate | Target |
| --- | --- |
| A1, A2 | Positive control |
| A3, A4 | C5a |
| A5, A6 | CD40 ligand |
| A7, A8 | G-CSF |
| A9, A10 | GM-CSF |
| A11, A12 | GROα |
| A13, A14 | I-309 |
| A15, A16 | sICAM-1 |
| A17, A18 | IFN-γ |
| A19, A20 | Positive control |
| B3, B4 | IL-1α |
| B5, B6 | IL-1β |
| B7, B8 | IL-1ra |
| B9, B10 | IL-2 |
| B11, B12 | IL-4 |
| B13, B14 | IL-5 |
| B15, B16 | IL-6 |
| B17, B18 | IL-8 |
| C3, C4 | IL-10 |
| C5, C6 | IL-12 P70 |
| C7, C8 | IL-13 |
| C9, C10 | IL-16 |
| C11, C12 | IL-17 |
| C13, C14 | IL-17E |
| C15, C16 | IL-23 |
| C17, C18 | IL-27 |
| D3, D4 | IL-32α |
| D5, D6 | IP-10 |
| D7, D8 | I-TAC |
| D9, D10 | MCP-1 |
| D11, D12 | MIF |
| D13, D14 | MIP-1α |
| D15, D16 | MIP-1β |
| D17, D18 | Serpin E1 |
| E1, E2 | Positive control |
| E3, E4 | RANTES |
| E5, E6 | SDF-1 |
| E7, E8 | TNF-α |

TABLE 1-continued

| Coordinate | Target |
|---|---|
| E9, E10 | sTREM-1 |
| E19, E20 | Negative control |

As seen from the table, treatment of the THP-1 cells with LPS and IFN-γ resulted in the increase of a total of 16 kinds of cytokines, GROα, I-309, sICAM-1, IL-1β, IL-1ra, IL-6, IL-8, IL-23, IP-10, MCP-1, MIF, MIP-1α, MIP-1β, serpin E1, RANTES and TNF-α. Accordingly, it can be seen that various inflammatory cytokines are produced in the THP-1 cells when they are treated with LPS and IFN-γ.

Test Example 4

Confirmation of Production of MMP-1 in THP-1 Cell Culture Medium

The following experiment was conducted to confirm the production of MMP-1 in a THP-1 cell culture medium treated with a stimulant.

THP-1 cells (acquired from Korean Cell Line Bank) were seeded onto a 6-well plate, with $5 \times 10^5$ cells per well, and cultured in an RPMI-1640 medium (acquired from Lonza) containing 10% (v/v) FBS, 100 U/mL penicillin and 100 μg/mL streptomycin under the condition of 37° C. and 5% $CO_2$ for 24 hours. Also, normal human fibroblasts (NHF cells, acquired from Lonza) were seeded onto a 24-well plate, with $3 \times 10^4$ cells per well, and cultured in a DMEM medium (acquired from Lonza) containing 10% (v/v) FBS, 100 U/mL penicillin and 100 μg/mL streptomycin under the condition of 37° C. and 5% $CO_2$ for 24 hours. The THP-1 cells were cultured in a medium treated with 1 μg/mL LPS (derived from E. coli 0111:B4, acquired from Sigma Aldrich) and 500 UNITs of IFN-γ (acquired from Sigma Aldrich) (stimulated medium) or with an untreated medium (non-stimulated medium) and the NHF cells were cultured in a serum-free medium for 24 hours. The THP-1 cell culture medium was centrifuged at 1000 rpm for 3 minutes and the supernatant was taken. The NHF cells treated with the non-stimulated THP-1 cell culture medium and the stimulated THP-1 cell culture medium were denoted as a non-stimulated medium treated group and a stimulated medium treated group, respectively, and those treated with serum-free DMEM was denoted as an untreated group. The concentration of MMP-1 in the NHF cells was measured using an MMP-1 assay kit and the ratio of the concentration of MMP-1 of the non-stimulated medium treated group and the stimulated medium treated group relative to the untreated group was calculated. The result is shown in FIG. 6.

Figure 6:
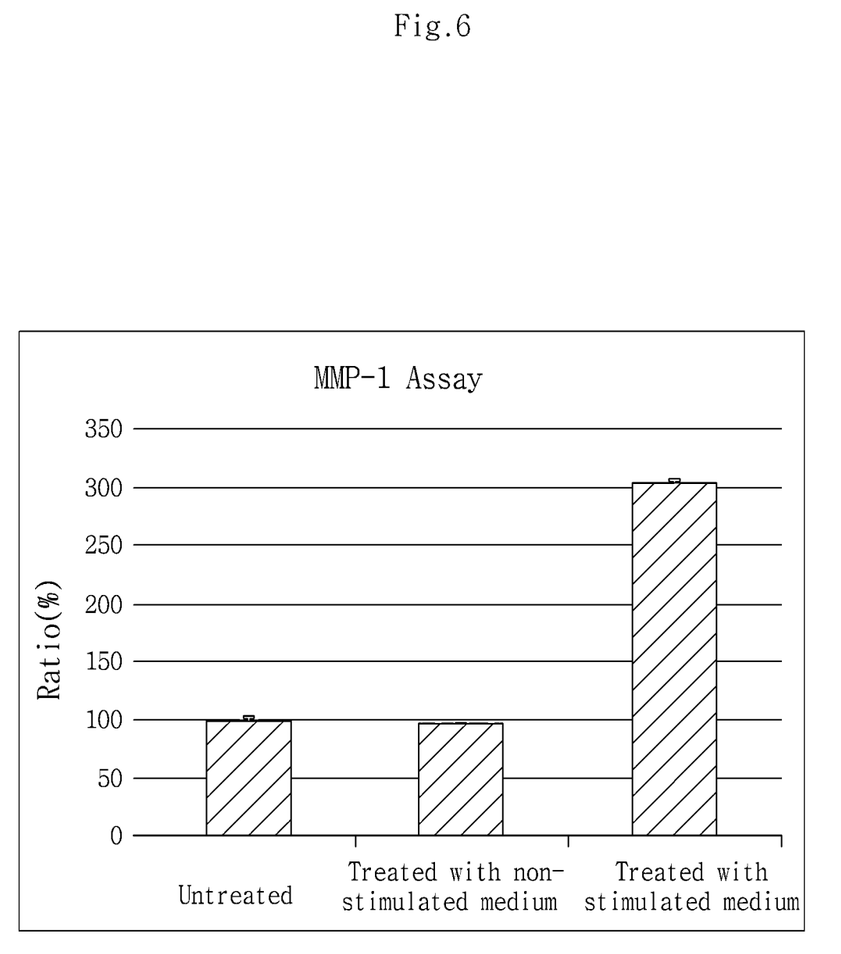
FIG. 6 shows the degree of production of MMP-1 in an NHF cell by a THP-1 cell treated with LPS and INF-γ.

As seen from FIG. 6, the non-stimulated medium treated group shows an MMP-1 concentration similar to that of the untreated group. In contrast, the stimulated medium treated group shows about 3 times higher MMP-1 production as compared to the untreated group. That is to say, since the THP-1 cell culture medium treated with the stimulant contains various inflammatory cytokines, the production of MMP-1 can be confirmed in the NHF cells.

Test Example 5

Determination of Optimal Concentration for Complex Treatment with Screening Candidate Substance and Stimulant The following experiment was conducted to determine the optimal concentration for complex treatment with a candidate substance to be screened for inhibition of inflammatory skin aging and a stimulant.

THP-1 cells (acquired from Korean Cell Line Bank) were seeded onto a 96-well plate, with $3 \times 10^4$ cells per well, and cultured in an RPMI-1640 medium (acquired from Lonza) containing 10% (v/v) FBS, 100 U/mL penicillin and 100 μg/mL streptomycin under the condition of 37° C. and 5% $CO_2$ for 24 hours. The cells were cultured for 24 hours after treating with 0.001, 0.01, 0.1, 1 and 10 μM glycitein which is known as a substance inhibiting inflammatory skin aging, as a screening candidate substance, and optionally with 1 μg/mL LPS (derived from E. coli 0111:B4, acquired from Sigma Aldrich) and 500 UNITs of IFN-γ (acquired from Sigma Aldrich) as stimulants. After treating with a cell counting kit reagent, with ⅒ the volume of each well, and culturing for 2 hours, O.D. value was measured using SpectraMax. Viability relative to the control group is shown in FIG. 7 and FIG. 8.

Figure 7:
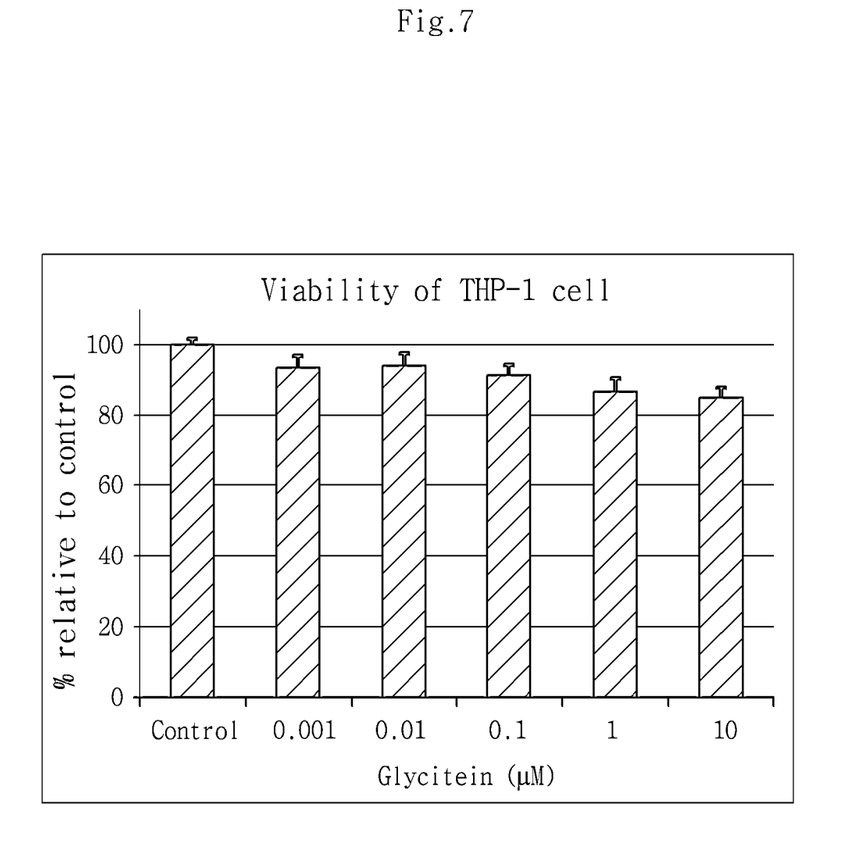
FIG. 7 shows the viability of a THP-1 cell treated with glycitein.
Figure 8:
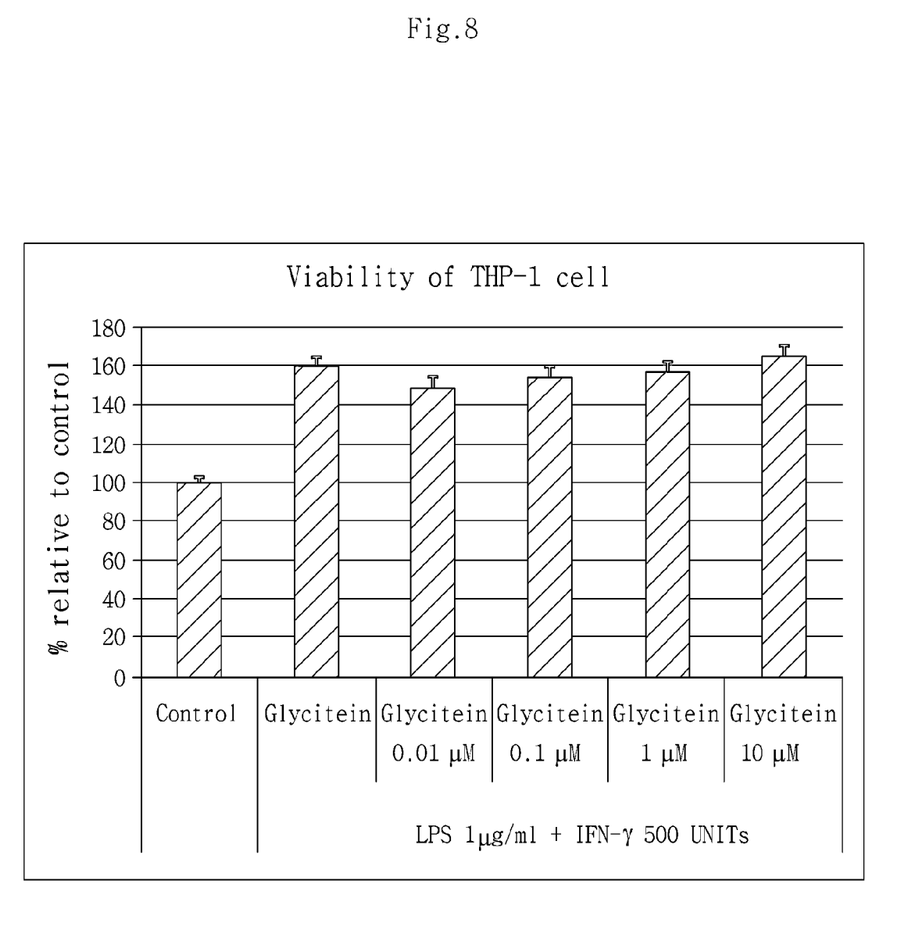
FIG. 8 shows the viability of a THP-1 cell treated with glycitein, LPS and INF-γ.

As seen from FIG. 7, no cytotoxicity was observed at glycitein concentrations 10 μM or lower. And, as seen from FIG. 8, no cytotoxicity was observed when glycitein was treated together with the stimulants LPS and IFN-γ.

Test Example 6

Confirmation of Production of TNF-α After Treatment with Screening Candidate Substance and Stimulant The following experiment was conducted to confirm the production of TNF-α upon treatment with a candidate substance to be screened for inhibition of inflammatory skin aging and a stimulant.

THP-1 cells (acquired from Korean Cell Line Bank) were seeded onto a 6-well plate, with $5 \times 10^5$ cells per well, and treated with 0, 0.1, 1 and 10 μM glycitein. The cells were cultured in an RPMI-1640 medium (acquired from Lonza) containing 10% (v/v) FBS, 100 U/mL penicillin and 100 μg/mL streptomycin under the condition of 37° C. and 5% $CO_2$ for 24 hours and then treated with 1 μg/mL LPS (derived from E. coli 0111:B4, acquired from Sigma Aldrich) and 500 UNITs of IFN-γ (acquired from Sigma Aldrich) as stimulants. After culturing for 24 hours, the culture medium was centrifuged at 1000 rpm for 3 minutes and the supernatant was taken. The concentration of TNF-α in the culture medium was determined using a TNF-α ELISA kit. The result is shown in FIG. 9.

Figure 9:
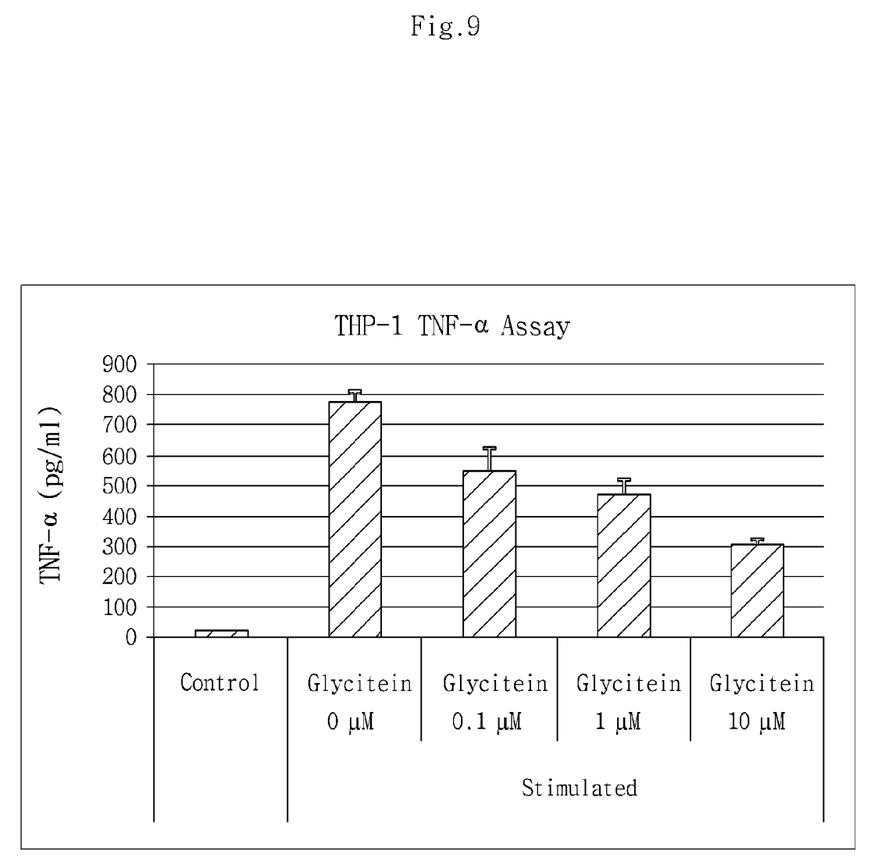
FIG. 9 shows the amount of production of TNF-α in a THP-1 cell treated with glycitein.

As seen from FIG. 9, the concentration of TNF-α was lower as the concentration of glycitein increased. In other words, the effect of inhibiting inflammation of a screening candidate substance can be determined by measuring the concentration of TNF-α.

Test Example 7

Confirmation of Production of Inflammatory Cytokines After Treatment with Screening Candidate Substance and Stimulant The following experiment was conducted to confirm the production of inflammatory cytokines upon treatment with a candidate substance to be screened for inhibition of inflammatory skin aging and a stimulant.

THP-1 cells (acquired from Korean Cell Line Bank) were seeded onto a 6-well plate, with $5 \times 10^5$ cells per well, and treated with 10 μM glycitein. The cells were cultured in an RPMI-1640 medium (acquired from Lonza) containing 10% (v/v) FBS, 100 U/mL penicillin and 100 μg/mL streptomycin under the condition of 37° C. and 5% $CO_2$ for 24 hours and then treated with 1 μg/mL LPS (derived from E. coli 0111:B4, acquired from Sigma Aldrich) and 500 UNITs of IFN-γ (acquired from Sigma Aldrich) as stimulants and cultured for 24 hours again. The cells untreated or treated only with the stimulant were used as a control group. The culture medium was centrifuged at 1000 rpm for 3 minutes and the supernatant was taken. The inflammatory cytokines included in the cell culture medium were identified using a cytokine array kit (R&D Systems). The amount of cytokines in the each treated groups relative to the positive control group is shown in FIG. 10.

Figure 10:
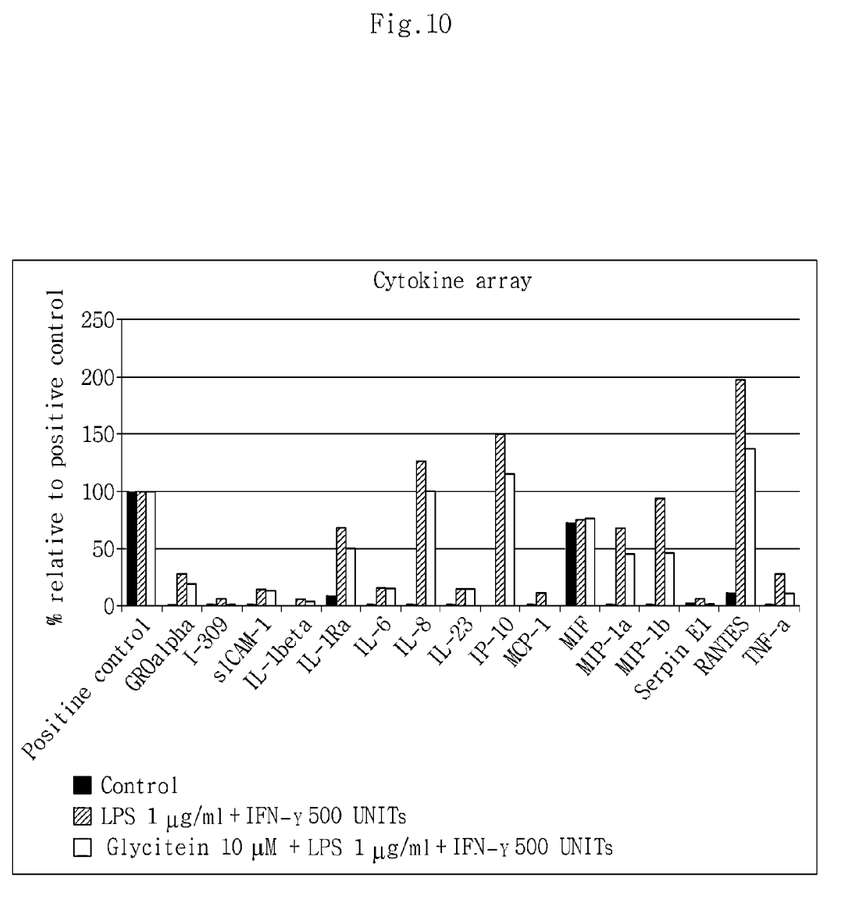
FIG. 10 shows the amount of production of an inflammatory cytokine when treated with glycitein and optionally with LPS and INF-γ.

As seen from FIG. 10, the amount of the inflammatory cytokines produced upon treatment with the stimulant is decreased by glycitein. In other words, the effect of inhibiting inflammation of a screening candidate substance can be determined by measuring the concentration of inflammatory cytokines.

Test Example 8

Determination of Optimal Concentration for Complex Treatment with Screening Candidate Substance and Stimulant The following experiment was conducted to determine the optimal concentration for complex treatment with a candidate substance to be screened for inhibition of inflammatory skin aging and a stimulant.

NHF cells (acquired from Lonza) were seeded onto a 96-well plate, with $1\times10^4$ cells per well, and cultured in a DMEM medium (acquired from Lonza) containing 10% (v/v) FBS, 100 U/mL penicillin and 100 μg/mL streptomycin under the condition of 37° C. and 5% $CO_2$ for 24 hours. The cells were cultured for 24 hours after treating with 1 μg/mL LPS (derived from *E. coli* 0111:B4, acquired from Sigma Aldrich) and 500 UNITs of IFN-γ (acquired from Sigma Aldrich) as stimulants and with 0, 0.1, 0.5, 1, 5 and 10 μM glycitein. After treating with a cell counting kit reagent, with 1/10 the volume of each well, and culturing for 2 hours, then O.D. value was measured using SpectraMax. Viability (%) relative to the negative control group is shown in FIG. 11.

Figure 11:
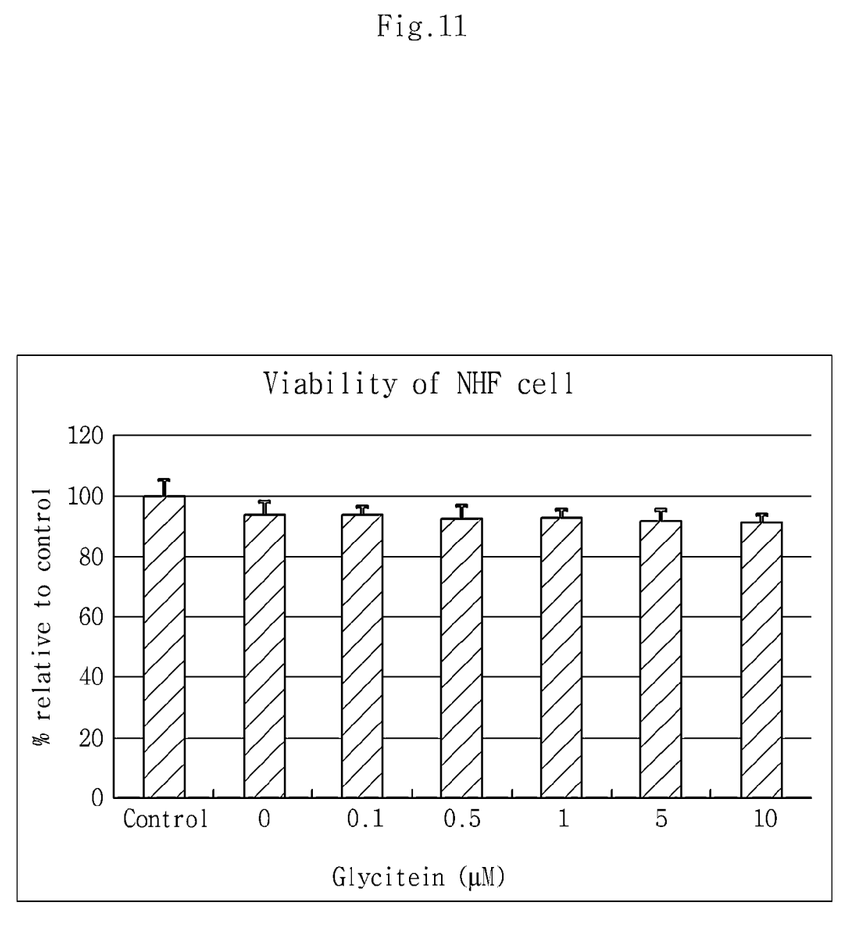
FIG. 11 shows the viability of a NHF cell treated with glycitein.

As seen from FIG. 11, no cytotoxicity was observed when glycitein, which is a substance inhibiting inflammatory skin aging, was treated together with the stimulants.

Test Example 9

Confirmation of Production of MMP-1 After Treatment with Screening Candidate Substance and Stimulant The following experiment was conducted to confirm the production of MMP-1 upon treatment with a candidate substance to be screened for inhibition of inflammatory skin aging and a stimulant.

THP-1 cells (acquired from Korean Cell Line Bank) were seeded onto a 6-well plate, with $5\times10^5$ cells per well, and cultured in an RPMI-1640 medium (acquired from Lonza) containing 10% (v/v) FBS, 100 U/mL penicillin and 100 μg/mL streptomycin under the condition of 37° C. and 5% $CO_2$ for 24 hours. Also, NHF cells (acquired from Lonza) were seeded onto a 24-well plate, with $3\times10^4$ cells per well, and cultured in a DMEM medium (acquired from Lonza) containing 10% (v/v) FBS, 100 U/mL penicillin and 100 μg/mL streptomycin under the condition of 37° C. and 5% $CO_2$ for 24 hours. The THP-1 cells were cultured in a medium treated with 1 μg/mL LPS (derived from *E. coli* 0111:B4, acquired from Sigma Aldrich) and 500 UNITs of IFN-γ (acquired from Sigma Aldrich) (stimulated medium) or with an untreated medium (non-stimulated medium) and the NHF cells were cultured for 24 hours in a serum-free medium treated with 10 μM glycitein. The THP-1 cell culture medium was centrifuged at 1000 rpm for 3 minutes and the supernatant was taken. The NHF cells were treated with the supernatant. NHF cells treated with serum-free DMEM (acquired from Lonza) were used as an untreated group. After culturing for 24 hours, the concentration of MMP-1 in the NHF cells was measured using an MMP-1 assay kit and the ratio of the concentration of MMP-1 relative to the untreated group was calculated. The result is shown in FIG. 12.

Figure 12:
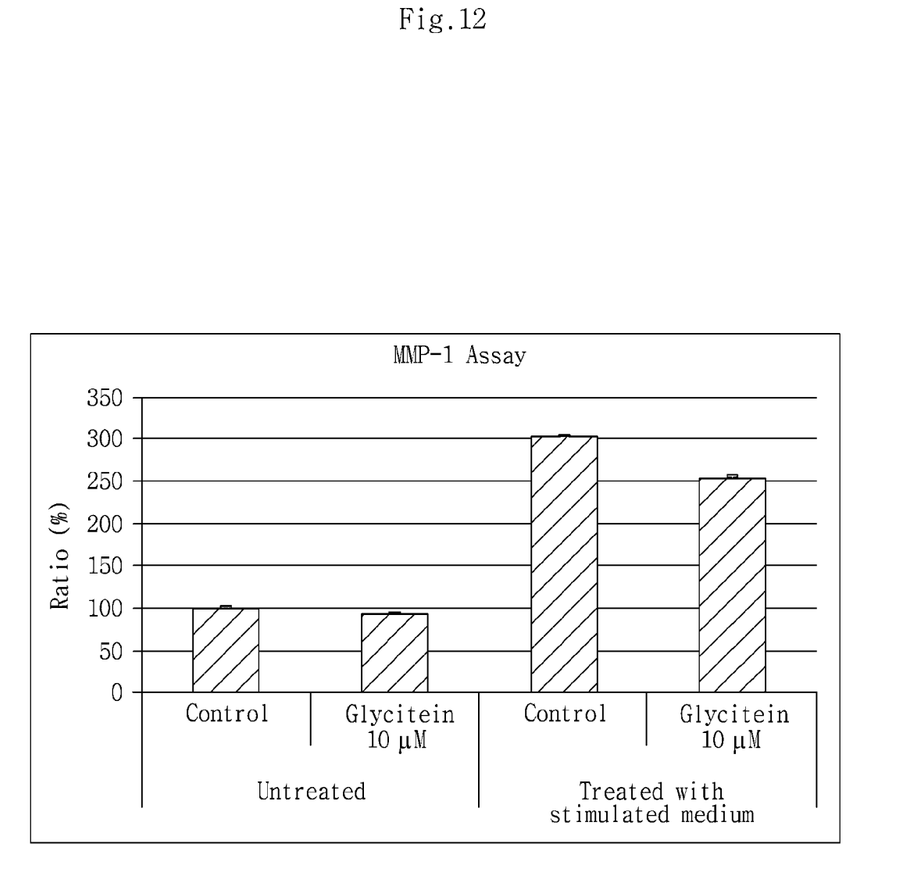
FIG. 12 shows the amount of production of MMP-1 in a THP-1 cell treated with LPS and INF-γ and in an NHF cell treated with glycitein.

As seen from FIG. 12, about 3 times more MMP-1 was produced in the stimulated medium than in the untreated medium. In addition, the treatment with glycitein resulted in decreased production of MMP-1.

If a certain substance can inhibit the production of MMP-1 induced by a stimulant, it means that the degradation of collagen due to inflammation can be inhibited and inflammatory skin aging can be inhibited. In other words, by confirming whether the production of MMP-1 in a skin cell is inhibited after treating with a candidate substance to be screened for inhibition of inflammatory skin aging, it can be determined whether the candidate substance can inhibit inflammatory skin aging. Since inhibition of MMP-1 production induced by several inflammatory cytokines, not by a particular inflammatory cytokine, a substance inhibiting inflammatory skin aging can be judged at once and can be screened more conveniently and effectively.

The invention claimed is:

1. A method for screening a substance inhibiting inflammatory skin aging, comprising steps of:
    a) treating an immune cell with an inflammatory stimulant;
    b) treating a skin cell with a candidate substance;
    c) treating the skin cell treated with the candidate substance, with the immune cell treated with the inflammatory stimulant;
    d) measuring a concentration of matrix metalloproteinase-1 (MMP-1) in the skin cell treated with the immune cell; and
    e) identifying the candidate substance as a substance inhibiting inflammatory skin aging if the concentration of the MMP-1 in the skin cell treated with the candidate substance is lower than the concentration of the MMP-1 in the skin cell not treated with the candidate substance.

2. The method for screening a substance inhibiting inflammatory skin aging according to claim 1, wherein the immune cell of the step a) comprises a THP-1 cell (human acute monocytic leukemia cell).

3. The method for screening a substance inhibiting inflammatory skin aging according to claim 1, wherein the skin cell of the step b) comprises a normal human fibroblast (NHF).

4. The method for screening a substance inhibiting inflammatory skin aging according to claim 1, wherein the inflammatory stimulant of step a) comprises comprises a lipopolysaccharide (LPS) and interferon-γ (INF-γ).

5. The method for screening a substance inhibiting inflammatory skin aging according to claim 4, wherein the LPS comprises an LPS derived from *Escherichia coli*.

6. The method for screening a substance inhibiting inflammatory skin aging according to claim 4, wherein a concentration of the LPS is 0.001-20 .mu.M and and amount of the INF-.gamma. is 1-2000 UNITs.

7. The method for screening a substance inhibiting inflammatory skin aging according to claim 1, in the step e), if the concentration of the MMP-1 in the skin cell treated with the candidate substance is lower compared to the concentration of the MMP-1 in the skin cell not treated with the candidate substance, such candidate substance would be identified as having a higher effect of inhibiting inflammatory skin aging.

* * * * *